(12) United States Patent
Aceto et al.

(10) Patent No.: US 11,452,543 B2
(45) Date of Patent: Sep. 27, 2022

(54) DEVICE AND METHOD FOR COMMINUTION OF CIRCULATING TUMOR CELL CLUSTERS

(71) Applicants: Griesmühle Kleinkraftwerk GmbH, Walding (AT); Universität Basel, Basel (CH); Johannes Kepler Universität Linz, Vienna (AT)

(72) Inventors: Nicola Aceto, Reinach (CH); Werner Baumgartner, Linz (AT); Kurt Priesner, Walding (AT)

(73) Assignees: Griesmühle Kleinkraftwerk GmbH, Walding (AT); Universität Basel, Basel (CH); Johannes Kepler Universität Linz, Vienna (AT)

( * ) Notice: Subject to any disclaimer, the term of this patent is extended or adjusted under 35 U.S.C. 154(b) by 34 days.

(21) Appl. No.: 16/078,705

(22) PCT Filed: Jun. 6, 2018

(86) PCT No.: PCT/EP2018/064935
§ 371 (c)(1),
(2) Date: Aug. 22, 2018

(87) PCT Pub. No.: WO2019/015854
PCT Pub. Date: Jan. 24, 2019

(65) Prior Publication Data
US 2021/0196309 A1   Jul. 1, 2021

(30) Foreign Application Priority Data

Jul. 17, 2017   (WO) ................ PCT/EP2017/068024

(51) Int. Cl.
*A61B 17/3207*  (2006.01)
*A61B 17/00*  (2006.01)

(52) U.S. Cl.
CPC ........... *A61B 17/320758* (2013.01); *A61B 2017/00398* (2013.01); *A61B 2017/320775* (2013.01)

(58) Field of Classification Search
CPC ........ A61B 17/320758; A61M 60/216; A61M 60/221; A61M 60/226; A61M 60/232; A61M 60/258; A61M 60/295
See application file for complete search history.

(56) References Cited

U.S. PATENT DOCUMENTS

| | | | |
|---|---|---|---|
| 2013/0338559 A1* | 12/2013 | Franano | .............. A61M 1/3655 604/4.01 |
| 2016/0331378 A1 | 11/2016 | Nitzan et al. | |
| 2017/0112986 A1 | 4/2017 | Hearing et al. | |

FOREIGN PATENT DOCUMENTS

DE    102004054714 A1    5/2006

OTHER PUBLICATIONS

Impella Cardiosystems GmbH, DE102004054714A1, English Abstract Translation, "Foldable Intravascularly Insertable Blood Pump", May 24, 2006 (13 pages).

(Continued)

*Primary Examiner* — Tuan V Nguyen
(74) *Attorney, Agent, or Firm* — McKee, Voorhees & Sease, PLC (57) ABSTRACT

Device and method for comminution or inactivation of circulating tumor cells (CTC) or tumor cell clusters (CTCC) from a tumor-affected organ or organ part, wherein it is proposed that in the venous drain of the tumor-affected organ or organ part a pump (2) with a pressure-increasing section and a pressure-reducing throttle (13) is arranged and is operated at the output side in its design point given by volumetric flow (Q) and pumping pressure (p) according to the volumetric flow and the blood pressure of the venous drain of the tumor-affected organ or organ part. Circulating (Continued)

tumor cells (CTC) and tumor cell clusters (CTCC) are thus comminuted and inactivated to thus reduce the risk of metastasis formation in cancerous diseases.

16 Claims, 8 Drawing Sheets

(56) References Cited

OTHER PUBLICATIONS

"The International Search Report and Written Opinion of the International Searching Authority", in connection to PCT/EP2017/068024 filed Jul. 17, 2017 dated Jan. 16, 2018 (13 pages).

* cited by examiner

DEVICE AND METHOD FOR COMMINUTION OF CIRCULATING TUMOR CELL CLUSTERS

CROSS-REFERENCE TO RELATED APPLICATION

This application claims benefit under 35 U.S.C. § 119 or § 120 to PCT/EP2017/06824, filed Jul. 17, 2017, herein incorporated by reference in its entirety.

BACKGROUND OF THE INVENTION

The present invention relates to a device and a method for the comminution or inactivation of circulating tumor cells (CTC) or tumor cell clusters (CTC clusters, CTCC) from a tumor-affected organ or organ part. The device according to the invention and the method according to the invention serve to reduce the risk of metastasis formation in cancers.

When the term "tumor" is used below for the sake of simplicity and comprehensibility, it also means all other cancers of organs of the human or animal body, even if these do not form as a circumscribed solid (solid) tumor.

It is known that in cancerous diseases primary tumors secrete cancer cells and the thus emitted cancer cells enter the bloodstream and circulate in the diseased body. These cancer cells are referred to below as circulating tumor cells, or as CTCs (circulating tumor cells). By definition, these are cells of the primary tumor or of metastases that have left the cell structure and are now in the blood circulation. The tumor cells thus circulating through the bloodstream in the body can now in turn settle in other tissue and there lead to the formation of secondary tumors, so-called metastases. This metastasis formation is a major problem in cancerous diseases. In the vast majority of fatal cancer cases, it is not the primary tumor that is causative for the death of the patient, but the metastases.

Current treatments aim to destroy the primary tumor, thereby suppressing the spread of circulating tumor cells and thus reducing the risk of metastasis. If the primary tumor is surgically removed in a surgical procedure, such an intervention always involves the risk of injury to the tumor tissue and the blood vessels present in the tumor tissue and the surrounding tissue with a corresponding release of tumor cells into the bloodstream and an associated increase in the risk of metastasis.

Studies in human cancer patients suggest that in advanced cancer, circulating tumor cells still occur in very low concentrations. The estimates here are about $2.5 \times 10^4$ tumor cells circulating in the blood of a patient with advanced cancer, which is approximately equivalent to a circulating tumor cell among 109 blood cells.

The existence of circulating tumor cells has been known for several decades, and the methods for isolating and examining these tumor cells have been increasingly improved. In this case, it turned out that circulating tumor cells can not only occur as single cells but also as cell aggregates of several tumor cells. These multicellular cell aggregates of circulating tumor cells are also referred to as circulating tumor cell clusters (CTC clusters, CTCC). Although circulating tumor cell clusters are less common than circulating tumor cells, they appear to be up to 50 times more likely to form metastases than single tumor cells. The probability of forming a metastasis thus seems to depend significantly on the number of these tumor cell clusters circulating in the blood. Aceto et al. were able to show that circulating tumor cell clusters originate from oligoclonal tumor cell aggregates and are not due to intravascular aggregation (Aceto, et al.: *Circulating Tumor Cell Clusters Are Oligoclonal Precursors of Breast Cancer Metastasis*; Cell 158, 1110-1122, 28 Aug. 2014).

The observation that tumor cell clusters could be found in blood from the arm vein of cancer patients also suggested that clusters might be able to cross capillary vessels. Indeed, Au et al. were able to show that clusters of circulating tumor cells are capable of traversing vessels with capillary-like dimensions, which has hitherto been considered impossible (Sam H. Au et al.: "*Clusters of circulating tumor cells traverse capillary-sized vessels*". Proceedings of the National Academy of Sciences, 2016; 201524448 DOI: 10.1073/pnas.1524448113). They used a microfluidic device with channels for this purpose, which narrowed to a size of 5-10 microns, which corresponds approximately to the dimensions of the smallest blood vessels of the human body. It could be shown that when using tumor cell clusters isolated from blood samples from cancer patients, clusters with a cell count of 20 cells or more could traverse even the smallest dimensions of the device without being retained in the microchannels. More detailed studies have shown that tumor cell clusters initially present as cell clusters in tight channels can adopt a chain-like configuration of juxtaposed cells in order to reorganize, after crossing the bottleneck, into a bulk-like cluster, apparently undamaged for further proliferation. The cells of the tumor cell cluster appear to adhere to each other through cell-cell interactions of different strengths, thereby temporarily relinquishing weaker interactions and maintaining stronger interactions during the presence of a chain-like configuration. The speed with which clusters were able to overcome a bottleneck did not depend on the initial size of the cluster, but on the size of the largest cell in the cluster, which fits this idea.

These observations confirm the potential of circulating tumor cell clusters to move in the bloodstream and lead to the formation of metastases. Studies such as those of Aceto et al. also show that the likelihood of metastasis formation could be reduced if one were able to destroy circulating tumor cell clusters and/or inactivate circulating individual tumor cells. The "inactivation" of circulating tumor cells or tumor cell clusters means that they no longer show the ability for metastasis formation.

SUMMARY OF THE INVENTION

It is therefore the object of the invention to comminute circulating tumor cell clusters and convert them into circulating tumor single cells, as well as to inactivate circulating tumor cells, thereby reducing the risk of metastasis formation in cancerous diseases.

This object is achieved by the features of claim 1. Claim 1 provides a device for comminution or inactivation of circulating tumor cells (CTC) or tumor cell clusters (CTCC) from an organ or organ part affected by a tumor, which according to the invention is formed from a pump arranged inside an outer jacket tube, which has a pressure-increasing section and a pressure-reducing throttle arranged on the pump outlet, and corresponds on the output side in its design point given by volumetric flow (Q) and pumping pressure (p) to the volumetric flow and the blood pressure of the venous drain of the tumor-affected organ or organ part, wherein the pump is formed as a micro-axial pump with a sequence of pressure-increasing blades arranged along a screw shaft of the micro-axial pump, and the throttle is designed as a flow resistance radially projecting from the screw shaft of the micro-axial pump, which flow resistance has a cylindrical section which forms a circular-cylindrical annular gap with the outer jacket tube enclosing the throttle.

The object according to the invention is further achieved by the features of claim 7. Claim 7 provides a method for the comminution or inactivation of circulating tumor cells (CTC) or tumor cell clusters (CTCC) from a tumor-affected organ or organ part, wherein according to the invention it is proposed that in the venous drain of the tumor-affected organ or organ part, for the comminution or inactivating the circulating tumor cells (CTC) or tumor cell clusters (CTCC), a pump is arranged with a pressure-increasing section and a pressure-reducing throttle and is operated at the output side in its operating point given by volumetric flow and pumping pressure according to the volumetric flow and the blood pressure of the venous drain of the tumor-affected organ or organ part.

The invention is based on a comminution of the circulating tumor cell clusters and inactivation of individual circulating tumor cells by shear stresses, as are exerted in the device according to the invention on the conveyed medium, in the present case on the venous blood. Although the pump conveys the venous blood, it is not the task of the pump to change the volumetric flow or the pumping pressure at the pump outlet in comparison to the pump input, but to generate shear stresses. Shear stresses occur in any liquid that experiences a change in flow velocity. The shear rate represents the difference in the flow velocities of two liquid layers of a laminar flow as a function of their distance. If the liquid is considered to be a body which is arranged between two mutually displaced plates and is connected thereto by adhesion, said body will undergo deformation upon displacement of the plates. The force F required for this accelerates the mass of the body. Shear stress, also referred to as a shearing stress, is the force needed per surface area to produce this acceleration and thus deformation, and thus to achieve a given volumetric flow in a viscous fluid. It depends on the size of the displaced surface, the distance between the two surfaces and the dynamic viscosity of the liquid in between. Typical values for shear stresses in the venous circulation are 0.1-0.25 Pa.

Initial experimental studies by the inventors have shown that shear stresses in the range of 200-500 Pa that can be replicated in microfluidic devices allowed tumor cell clusters isolated from blood samples from cancer patients to be disrupted and converted into tumor single cells. In addition, even the destruction and thus inactivation of circulating single tumor cells could be observed.

Too high shear stresses could also act in a hemolytic way and thus damage blood components. It is known, for example, that the shear stress exerted on erythrocytes can indirectly influence the aggregation of platelets, which in turn is also shear-stress-dependent. Shear stress also causes a spindle-shaped deformation of the erythrocytes.

However, the shear stresses, which could lead to a comminution of tumor cell clusters as well as an inactivation of individual tumor cells in the experiment, seem to be sufficiently low so that the other blood components are not or hardly permanently damaged. It is assumed that unlike erythrocytes, leukocytes, platelets or endothelial cells which are adapted to hemodynamics, the mechanical properties of circulating tumor cells and tumor cell clusters are not perfectly matched to the flow in the vascular system and, in particular, have limited resistance to shear stress. This mechanical difference is used according to the invention therapeutically. In previously unpublished preliminary experiments with cultured tumor cells or tumor cell clusters, the inventors were able to demonstrate on the one hand that tumor cell clusters could be destroyed by temporally limited action of high liquid shear stress on tumor cell clusters so that only single cells are present. With even higher shear stress, even the circulating single tumor cells are destroyed. On the other hand, these experiments also showed that the destruction of the tumor cell clusters or the circulating tumor cells correlated directly with two parameters: on the one hand, the height of the liquid shear stress (the shearing stress) and, on the other hand, the duration of the shear stress. The exact structure and results of the experiments will be explained in more detail below. Under the same conditions, human blood was also subjected to shear stress by volunteer donors. Thereafter, the blood was examined. Both erythrocytes, leukocytes, platelets and their degradation products in the serum were quantified. No haemolysis could be detected in this case. Even under conditions where 90% of the circulating tumor cells were destroyed, no difference to non-sheared blood was detectable. It could thus be shown that a therapeutic window exists for shear stress in which circulating tumor cells and tumor cell clusters, but not the blood, are damaged.

According to the invention, this effect is exploited by reproducing shear stresses in the pump in the range of 200-500 Pa in order to destroy tumor cell clusters and convert them into tumor single cells. The method according to the invention now provides for such a placement in the vicinity of the tumor. Preferably, the pump is used concomitantly in a primary tumor removal operation to immediately disintegrate tumor cell clusters released during surgery into the bloodstream, thereby selectively reducing the risk of metastasis formation often associated with surgery. The pump may subsequently be removed at the conclusion of the surgery for surgical removal of the primary tumor, or may be left in the venous drain for a suitable period of time to be removed later.

Since the entry of any tumor cell clusters released into the bloodstream of the patient takes place via the venous drain of the tumor-affected organ or organ part, the pump is placed according to the invention in the venous drain of the affected organ or organ part. It thus concerns the low pressure area of the bloodstream. In the known manner, the pressure conditions in the bloodstream are very different. The heart works primarily as a press pump and less than a suction pump, where it presses an average of about 70 milliliters of blood from the left ventricle into the aorta in each ejection phase of heart-healthy adults. This amount of blood puts pressure on the blood column in the aorta or in the arteries departing therefrom. Thus, the blood is further "pushed" through the vascular system via the arterial limb of the capillary system into the venules and from there via the veins in the direction of the right atrium. The veins carry the blood from all organs and distant parts of the body back to the heart. The larger the diameter of the vein towards the heart, the lower the prevailing pressure. In a healthy, lying subject, the pressure in the capillary vein part is about 20 mmHg, decreases in the groin to about 8-12 mmHg, in the abdominal cavity (intra-abdominal) about 3-5 mmHg and in the right atrium only 2 mmHg.

In principle, within the scope of the method according to the invention, the aim is to place the device according to the invention as close as possible to the tumor-affected organ or organ part. Of course, the appropriate vein must be suitable for the appropriate placement of the pump in terms of size and accessibility. In addition, the physiological conditions or medical reasons can call for a particular location of placement of the pump according to the invention in venous drain of an organ or organ part. The hepatic portal vein (V. portae hepatis), the renal vein (V. renalis), the inferior vena cava (V. cava inferior) and the superior vena cava (V. cava superior) appear to be particularly suitable. In the case of the superior vena cava, placement of the pump according to the invention in the area of the venous angle (angulus venosus) in particular appears to be particularly advantageous, since the venous angle leads to the large lymphatic collection strains and thus the likelihood of lymphogenic metastasis can also be reduced. However, it is also conceivable to place several devices according to the invention at different locations in the venous drain of a tumor-affected organ or organ part.

Since the blood pressure in the veins is very low compared to the arteries, the veins have a much thinner wall than arteries. In addition, the blood in the veins flows very slowly due to the low blood pressure. Therefore, according to the invention, a pump is proposed which, in its design point given by volumetric flow and pumping pressure, corresponds to the volumetric flow and the blood pressure of the venous drain of the tumor-affected organ. As is known, each pump has a design point, which is generally defined by the required volumetric flow and the desired pumping pressure. Based on the thus predetermined design point and the medium to be delivered—in the present case blood—pump variables such as the diameter and length of the pump, the design of the rotor and the speed of the pump can subsequently be determined and the pump characteristic can be established for the pump in question, which determines the course of the volumetric flow as a function of the delivery pressure away from the design point.

In practical use, the pump is finally operated at a predetermined operating point, which usually corresponds to the design point. According to the invention, the pump is operated such that on the output side, in its operating point given by the volumetric flow Q and pumping pressure p, it corresponds to the volumetric flow and the blood pressure of the venous drain of the tumor-affected organ or organ part. After introduction of the pump according to the invention into the venous drain of the tumor-affected organ or body part, the blood is removed at the pump inlet and ejected at the pump outlet, but without changing the volumetric flow or the pumping pressure at the pump outlet compared to the pump inlet appreciably, this being in order to generate shear forces which destroy the circulating tumor cell clusters but do not damage the other blood components. In addition, care must be taken that the blood circulation of the patient's body is not adversely affected. Congestion and local or even systemic hypertension should be avoided at all costs. For this, the device must adapt to the local circulatory control in the body. Therefore, it is preferably proposed that in each case a pressure sensor is provided in front of the pump and after the throttle, and a control unit which regulates the pressure difference of the pressure values measured by the two pressure sensors by varying the rotational speed of the screw shaft to a predetermined setpoint value. In this case, the setpoint value specified for the pressure difference is preferably 0. Thus, the device according to the invention appears to be non-existent for the natural blood circulation. The function is expected to be available over a wide control range. This is, as was found in the above-mentioned preliminary experiments, because the destruction performance of the device according to the invention is dependent on the shear stress and on the dwell time on the rotating throttle. With increased blood flow, so that the differential pressure is kept at 0, the speed must be up-regulated. As a result, a higher amount is pumped through the pump, which thus reduces the dwell time on the throttle. At the same time, however, the shear stress increases. According to the invention this is ensured in that the pump is designed as a micro-axial pump with a sequence of pressure-increasing blades arranged along a screw shaft of the micro-axial pump, and the throttle as a flow resistance radially projecting from the propeller shaft of the micro-axial pump. The throttle and the micro-axial pump are thus forcibly guided in terms of their speed via the common screw shaft, i.e. the throttle and the micro-axial pump always rotate at the same speed. If the volumetric flow increases due to higher speed of the micro-axial pump, the dwell time decreases, but the shear stress especially in the annular gap between the throttle and the outer jacket tube increases due to the likewise higher speed of the throttle. If, on the other hand, the volumetric flow drops due to the lower speed of the micro-axial pump, the dwell time increases, but the shear stress, in particular in the annular gap between the throttle and the outer jacket tube, drops because of the likewise lower speed of the throttle. However, as long as the pump characteristic can be linearized with sufficient accuracy, the destructive effect remains approximately constant. In the aforementioned preliminary experiments, a rotating throttle with speed control and a separate, independently controllable pump was used. Thus, shear stress and dwell time could be adjusted independently. Essential for the design of the device according to the invention is also that the blood is always kept under pressure, since negative pressure leads to hemolysis. In addition, the shear stress should be as constant as possible in the area of the axial pump.

Since cavitation must be avoided at all costs, it is preferably proposed that a coaxial, inner jacket tube be provided inside the outer jacket tube and fastened to the blades of the micro-axial pump. This design has the advantage of a very even distribution of shear stress and prevents cavitation on the outside edges of the screw. The screw shaft extends in the axial direction beyond the axial extension of the inner jacket tube and converges into the pressure-reducing throttle in this area, which has a cylindrical section which forms a circular-cylindrical annular gap with the outer jacket tube surrounding the throttle.

Since the pump according to the invention is to be placed intracorporeally in the venous drain of an organ or organ part, correspondingly small dimensions are required, with corresponding pumps being referred to as micropumps. Structural designs of such micropumps are known per se for the field of cardiac assist systems in which implanted pumps are intended to support or even replace cardiac activity. In most cases, these are left heart assist systems (i.e. Left Ventricle Assist Devices—LVAD), where a pump pumps blood from the left heart chamber (the left ventricle) into the aorta. However, the design point and consequently the operating point of the pumps required here differ fundamentally from that of the pump provided according to the invention, since they are arranged in the high-pressure region of the blood circulation in known cardiac assist systems and designed for a higher volumetric flow and a higher pumping pressure.

In the context of the present invention, the volumetric flow Q of the pump is preferably 0.1-1.5 liters/minute and the pumping pressure p 4-20 hPa. These flow conditions occur in the venous drain of most organs of the human being. Therefore, the volumetric flow in the hepatic portal vein of an adult is about 0.8 l/min at a blood pressure of about 4-8 hPa, in the venous drain of the liver about 1.3 l/min and in the venous drain of the kidney about 0.5 l/min. In the venous blood circulation, the volumetric flow can also have significantly different values. Therefore, the volumetric flow in the upper vena cava is about 2 l/min, in the inferior vena cava about 3 l/min and in the pulmonary circulation up to 5 l/min. The precise value of the design point of the pump according to the invention thus depends on the volumetric flow and the pressure at the place of placement of the pump in the venous drain of the tumor-affected organ or organ part, as will be explained in more detail.

Since volumetric flow and blood pressure not only vary widely within the venous blood circulation of the same person, but also from person to person depending on age, weight or physical condition, it is conceivable to tailor the exact value of the design point of the pump according to the invention to a specific patient individually. Thus, on the one hand the exact caliber of the affected vessel, as well as the constitution of the patient and the individual cardiac output must be considered. Recent diagnostic methods allow the local determination of vessel diameter, blood pressure and volumetric flow at any point in the venous blood circulation, so that pinpoint local flow conditions can be determined. It is thus conceivable to use these measured values for determining the design point of the pump according to the invention and to subsequently design the pump based on the known shear stresses which must be ensured in the pump for comminuting and inactivating the tumor cells and tumor cell clusters. In order to be able to manufacture the device according to the invention in an individualized manner, additive and subtractive production methods can be used, for example in the form of 3D metal printing, so that manufacture of the critical components of the device according to the invention that are to be individually dimensioned is possible within a very short time.

BRIEF DESCRIPTION OF THE DRAWINGS

The invention will be explained in more detail below by means of embodiments with reference to the accompanying drawings, wherein.

DETAILED DESCRIPTION OF EXEMPLARY EMBODIMENTS ACCORDING TO THE INVENTION INVENTION

Figures 1, 2:
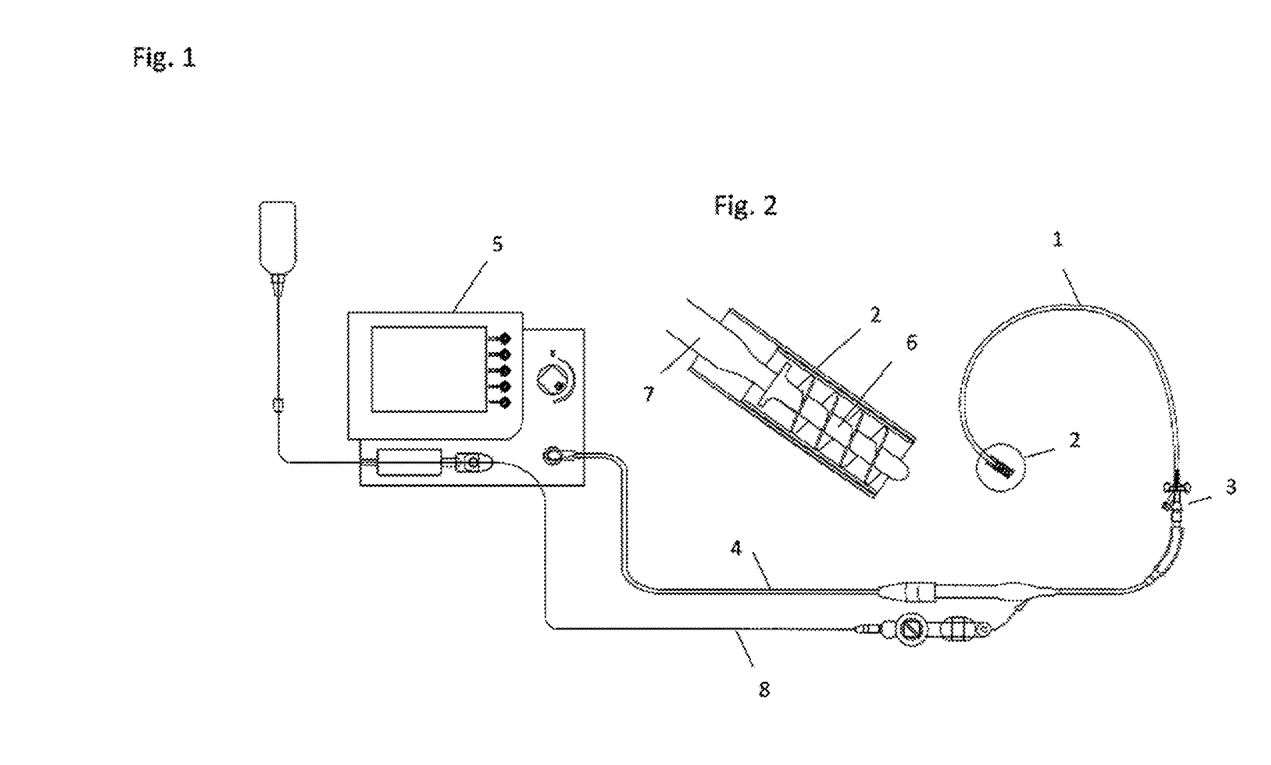
FIG. 1 shows a schematic representation of an embodiment of an arrangement for use of the device according to the invention in the context of the method according to the invention.
FIG. 2 shows a representation of a first embodiment of a micro-axial pump according to the invention with throttle.

Reference is first made to FIG. 1, which shows a schematic representation of an embodiment of a possible arrangement for application of the device according to the invention in the context of the method according to the invention. On the right side of FIG. 1, the flexible venous catheter 1 can be seen, at the free end of which the pump 2 according to the invention is arranged. The pump 2 is designed as a micro-axial pump and marked in FIG. 1 with a circle and shown enlarged in FIG. 2.

The venous catheter luer lock connection 3 is outside of the patient. At the luer lock connection 3, the connection line 4 is connected to the control and monitoring unit 5. Via the venous catheter 1 and the connecting line 4, an electrical connection 7 between the control and monitoring unit 5 and the pump 2 is laid (see also FIG. 2). By way of the control and monitoring unit 5, operating parameters such as the rotational speed of the screw shaft 6 of the pump 2 designed as a micro-axial pump can be controlled in this way. However, it would also be conceivable to carry out local venous pressure measurements via the venous catheter and to display the measured values via the control and monitoring unit 5. Optionally, an injection system 8 may be provided for the delivery of medicaments such as chemotherapeutic agents or blood thinners, or else for the delivery of glucose solutions and the like.

Alternatively, the pump 2 according to the invention could also be implanted by surgically inserting the pump 2 into the vein, or severing the vein at the site of the pump 2 and securing it to both sides of the pump 2.

Figure 3A:
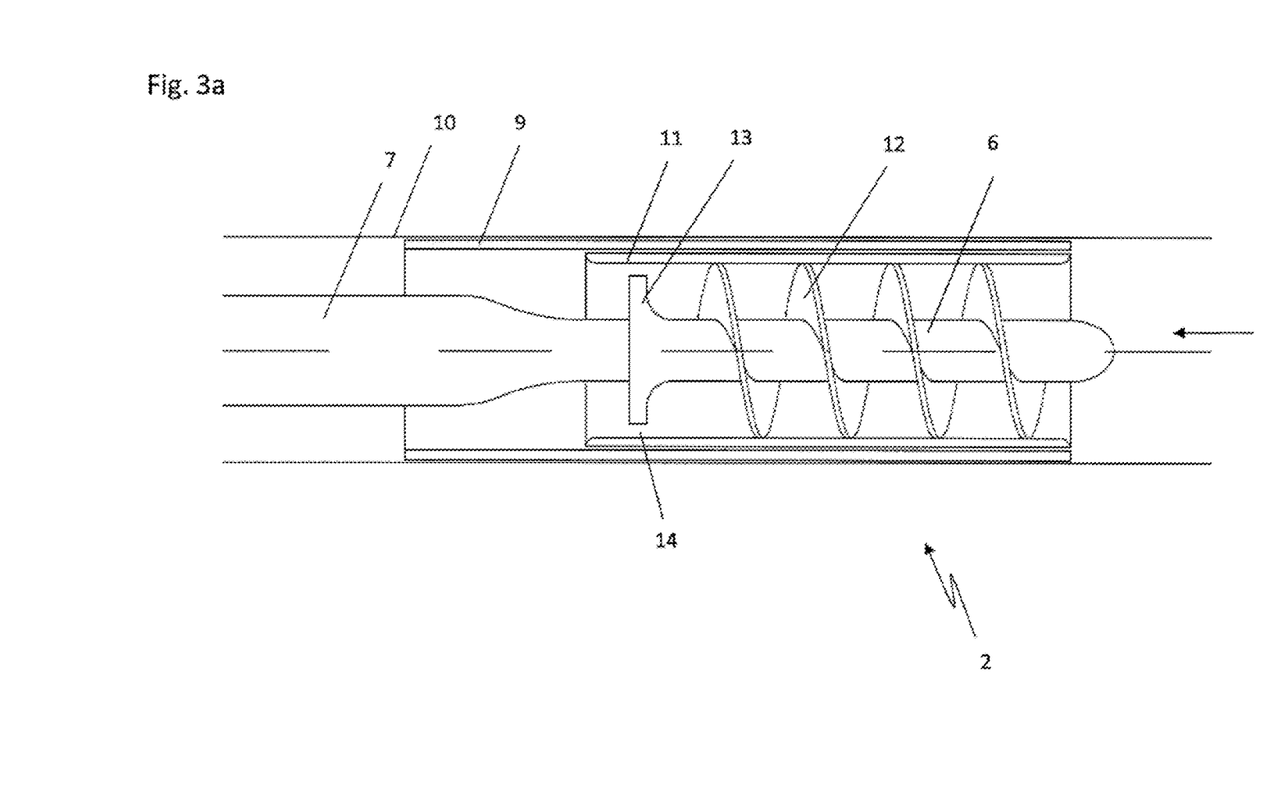
FIG. 3a shows an enlarged view of an embodiment of a micro-axial pump according to the invention with throttle according to FIG. 2.
Figure 3B:
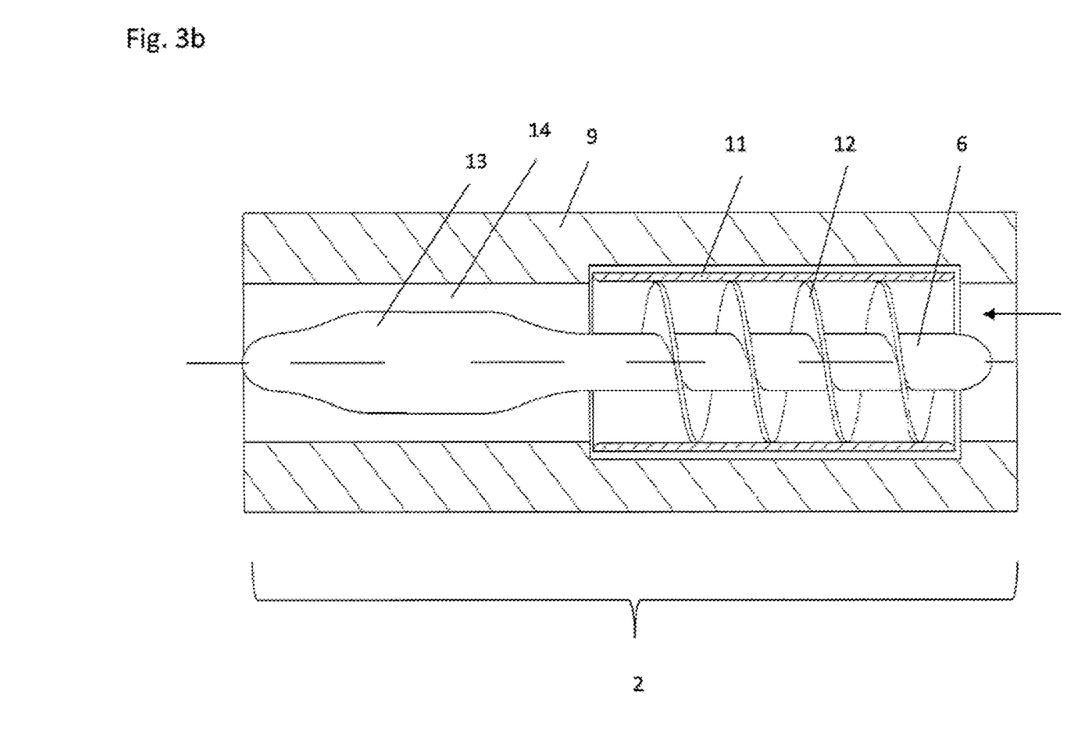
FIG. 3b shows a representation of a second embodiment of a micro-axial pump according to the invention with throttle.

Possible embodiments of the pump 2 designed as a micro-axial pump will be explained with reference to FIGS. 3a and 3b. According to the illustrated embodiments, an outer jacket tube 9 is provided, which is arranged stationary within the vein wall 10 at the intended site of placement of the micro-axial pump. An inner jacket tube 11 is fixed to the screw shaft 6 and/or the blades 12 of the micro-axial pump and rotates with the screw shaft 6. The screw shaft 6 is set in rotation by means of a drive (not shown in FIGS. 3a and 3b), which is supplied with power via the electrical connection 7. The inlet of the pump 2 is located on the right side with reference to FIGS. 3a and 3b, wherein the direction of flow of the venous blood is indicated by an arrow. The output of the pump 2 is located on the left side with reference to FIGS. 3a and 3b.

Since the venous wall 10 in the venous drain of an organ or organ part can sometimes be very thin and should not be damaged in the course of use of the pump 2 according to the invention, a pressure-reducing throttle 13 is arranged at the outlet of the pump 2. This measure also makes it possible to increase the pumping pressure p to increase the shear forces within the micro-axial pump 2 in a targeted manner, but nevertheless to ensure moderate pressure ratios on the pump outlet which are matched to the venous drain VA. The throttle 13 is designed as a flow resistance radially projecting from the screw shaft 6 of the pump 2, which has a cylindrical section which forms a circular-cylindrical annular gap 14 with the outer jacket tube 9 enclosing the throttle 13. In this annular gap 14 there is appropriate shear stress.

Figure 6:
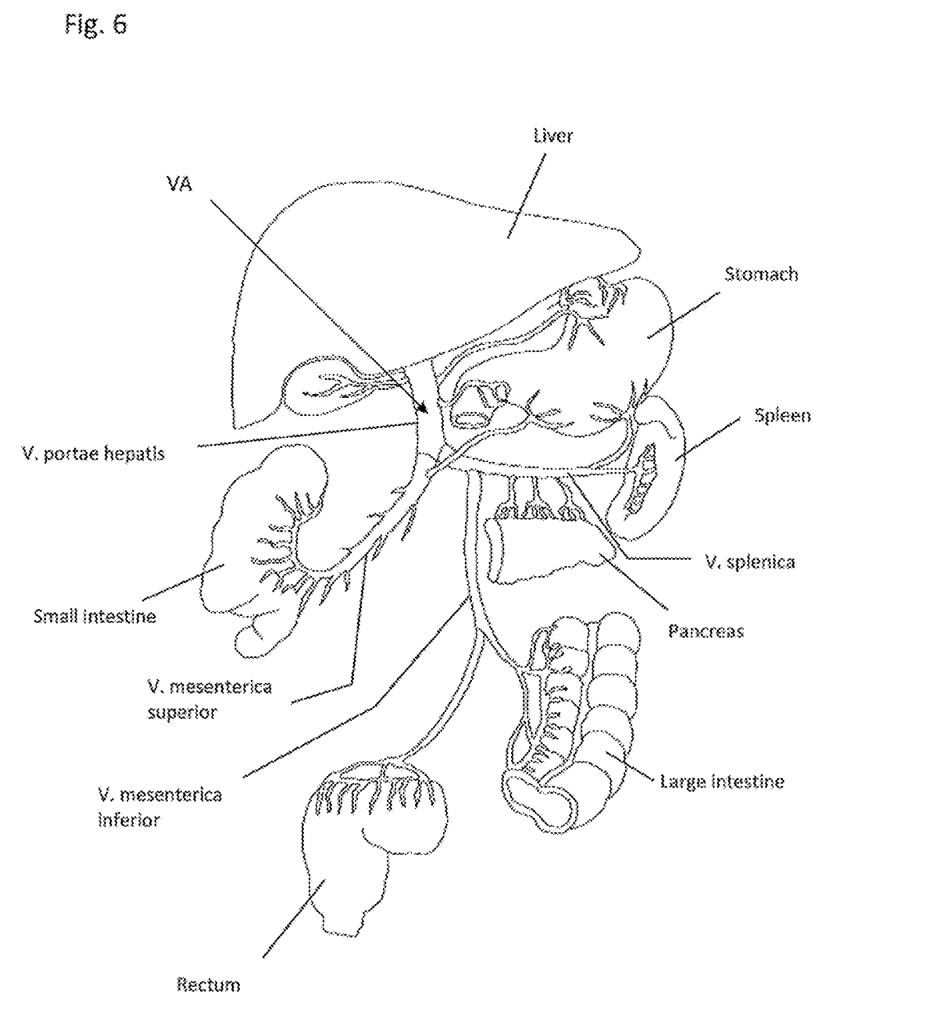
FIG. 6 shows a representation for explaining the placement of the device according to the invention in the context of the method according to the invention using the example of the digestive system.
Figure 7:
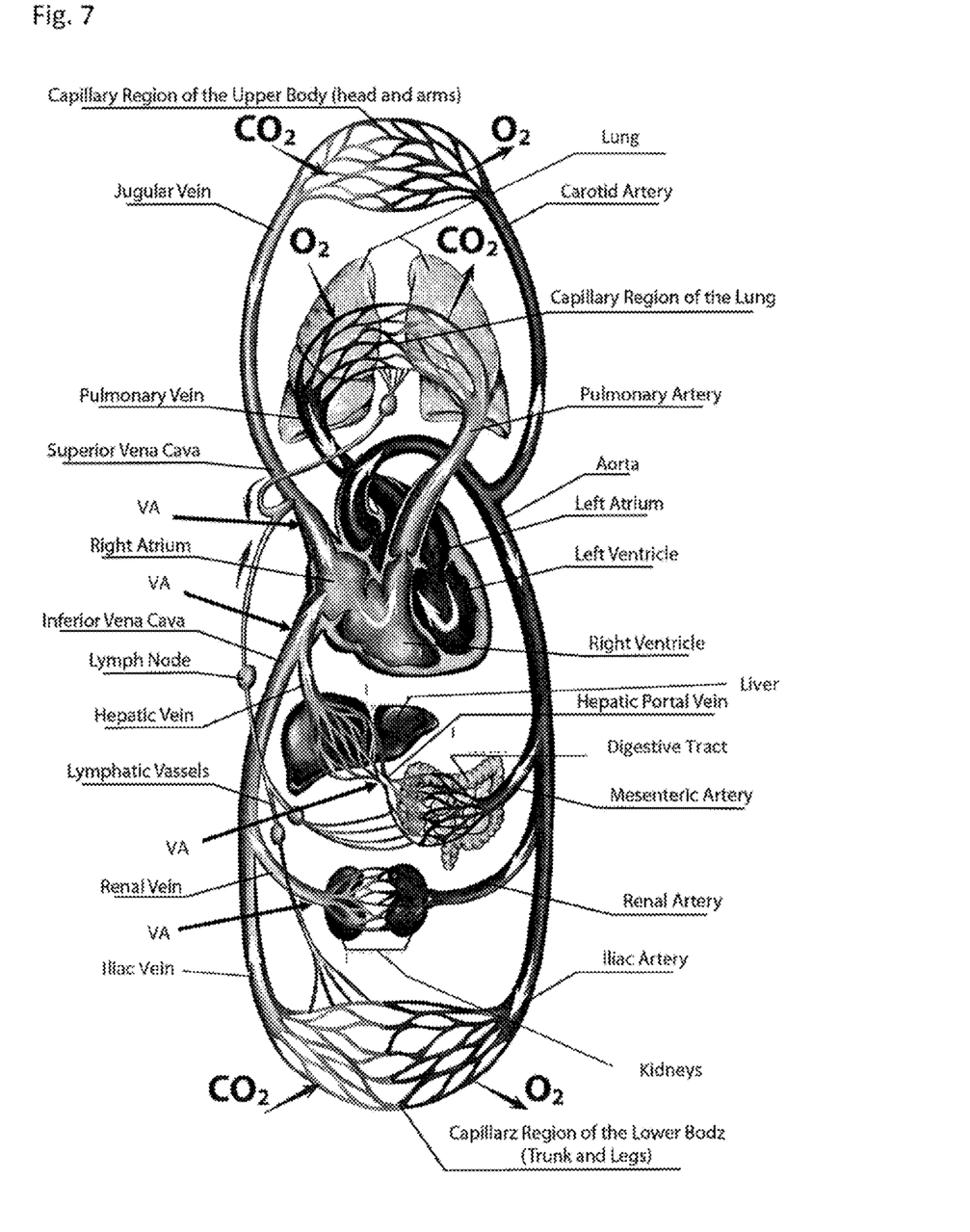
FIG. 7 shows a further representation to explain the placement of the device according to the invention in the context of the method according to the invention in the bloodstream.

The pump 2 according to the invention corresponds in its design point given by volumetric flow Q and pumping pressure p to the volumetric flow and the blood pressure of the venous drain VA of the tumor-affected organ (see also FIGS. 6 and 7). In the context of the present invention, the volumetric flow Q of the pump 2 is preferably 0.1-1.5 liters/minute and the pumping pressure p 4-20 hPa. The exact value of the design point depends on the volumetric flow and the pressure at the location of the pump 2 in the venous drain VA of the tumor-affected organ or organ part. The throttle 13 is of course taken into account in the choice of the design point of the pump 2, so that said values for the flow rate Q of the pump 2 of 0.1-1.5 liters/minute and the pumping pressure p of 4-20 hPa relate to the conditions after the throttle 13, as seen in the flow direction.

Figure 4A:
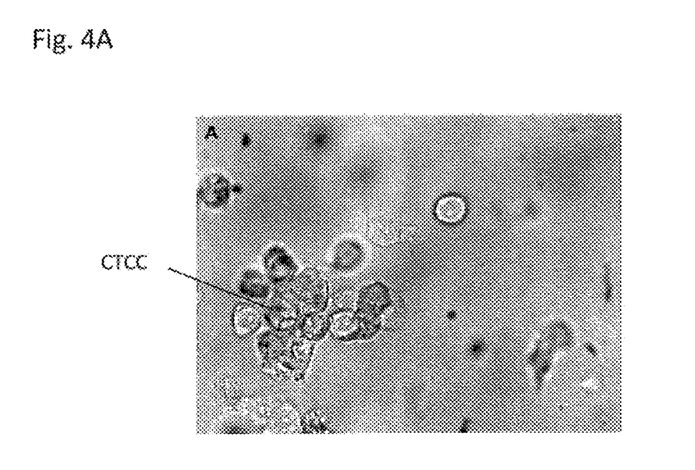
FIG. 4A shows a micrograph of a tumor cell cluster.
Figure 4B:
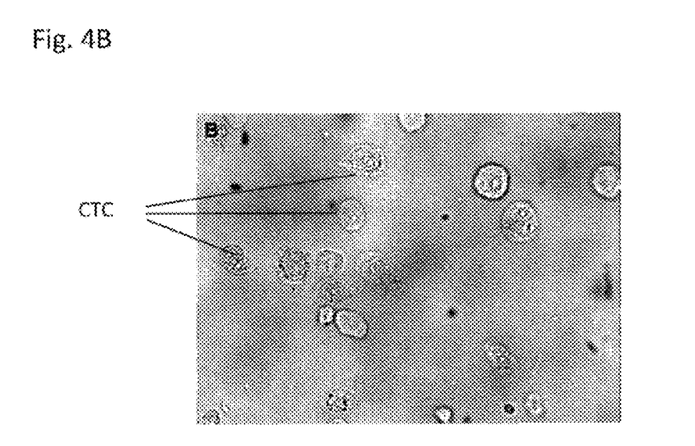
FIG. 4B shows a micrograph of the tumor cell cluster of FIG. 4A converted into tumor single cells after passing a microfluidic device at shear rates similar to those of the device according to the invention.

The basic operating principle of the device according to the invention and of the method according to the invention will be explained with reference to FIGS. 4 and 5. FIG. 4 shows experimental results for comminution of circulating tumor cell clusters CTCC by shear stress, wherein FIG. 4A is a micrograph of a tumor cell cluster CTCC isolated from blood samples from cancer patients before passing a microfluidic device at shear rates as simulated by the device of the invention; FIG. 4B is a micrograph of the tumor cell cluster CTCC of FIG. 4A converted into tumor single cells CTC after passing said microfluidic device. The comparison of FIG. 4A with FIG. 4B shows that it was possible to destroy tumor cell clusters CTCC and convert them into tumor single cells CTC. It should be noted that the individual tumor cells CTC touching in FIG. 4B move independently of one another as soon as the culture dish is moved, i.e. they do not adhere to one another. During an observation period of 60 minutes, no further aggregation of the individual tumor cells CTC to tumor cell cluster CTCC could be observed. On the other hand, the shear stresses, which could cause a comminution of tumor cell clusters CTCC in the experiment, were even low enough not to damage the other blood components. This therapeutic window is exploited by the device according to the invention and the method according to the invention.

Figure 5:
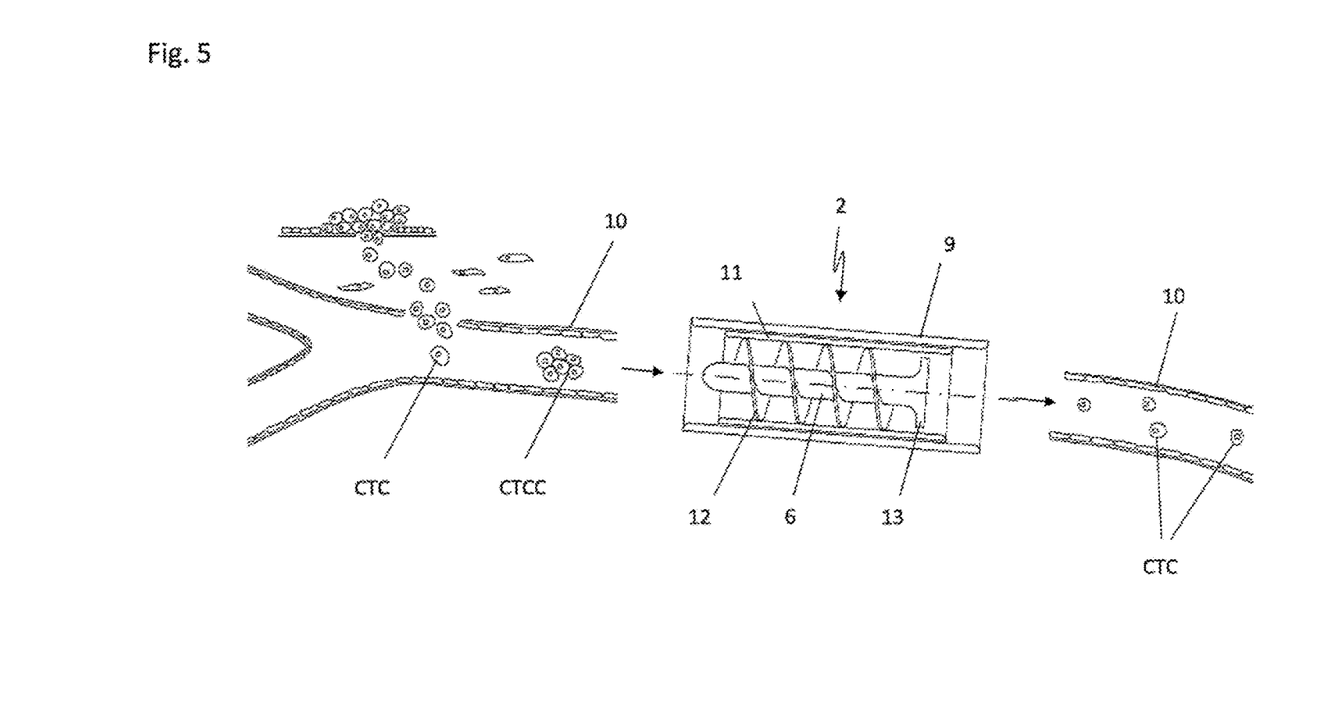
FIG. 5 shows a representation of the basic principle of operation of the device according to the invention and of the method according to the invention.

A model illustration of this process is shown in FIG. 5. On the left side of FIG. 5, the process is shown in which, in the course of the surgical removal of a primary tumor for example, tumor tissue and blood vessels existing in the tumor tissue and the surrounding tissue are injured, which may be associated with a corresponding release of circulating tumor cells CTC into the bloodstream and an associated increase in the risk of metastasis formation. The circulating tumor cells CTC can also be released as circulating tumor cell clusters CTCC and move in this configuration through the bloodstream. However, according to the invention, a pump 2 designed as a micro-axial pump is arranged in the venous drain VA of the tumor-affected organ (see also FIGS. 6 and 7), which exerts shear stresses on the ingredients contained in the blood, which do not damage the other blood components, but exert a degrading and thus inactivating effect on the circulating tumor cells CTC and tumor cell clusters CTCC. After passing through the pump 2, there are thus no more circulating tumor cell clusters CTCC in the bloodstream, but largely inactivated circulating tumor single cells CTC with a significantly lower risk of metastasis formation.

Figure 8A:
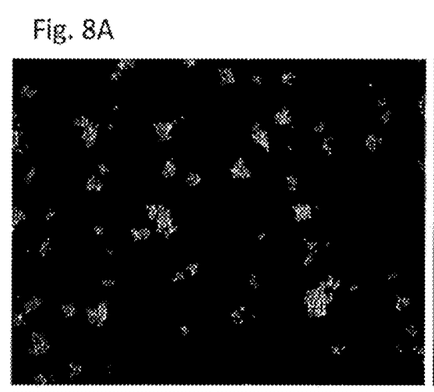
FIG. 8A shows a micrograph of cultured tumor cells (LM1 cells from a colon carcinoma) forming distinct tumor cell clusters in culture.
Figure 8B:
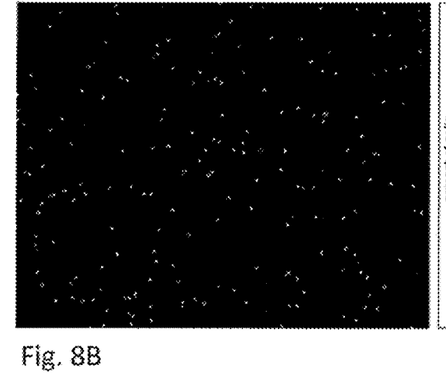
FIG. 8B shows a micrograph of cultivated tumor cells after a short application of shear stress, wherein practically only single cells are present.
Figure 8C:
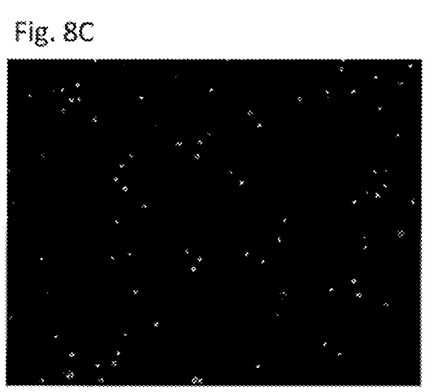
FIG. 8C shows a micrograph of cultivated tumor cells after application of a higher shear stress compared with FIG. 8B, wherein cell damage and thus the inactivation of individual tumor cells can be recognized.
Figure 8D:
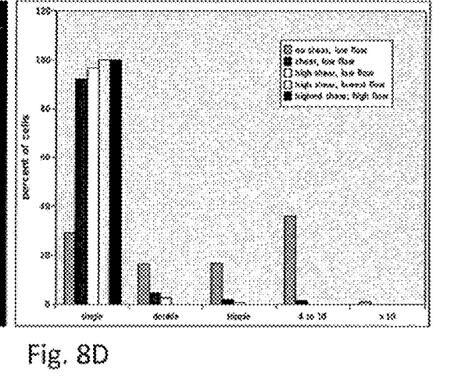
FIG. 8D shows a summary of different experiments, wherein in particular the percentage of all microscopically visible particles is shown according to the number of cells of which they consist.

For this purpose, FIG. 8A shows a micrograph of cultivated tumor cells (LM1 cells from a colon carcinoma), which form clearly recognizable tumor cell clusters in the culture. FIG. 8B shows a micrograph of cultivated tumor cells after a short application of shear stress, wherein practically only single cells are present. FIG. 8C shows a micrograph of cultivated tumor cells after application of a shear stress which is higher relative to FIG. 8B, wherein cell damage and thus the inactivation of individual tumor cells can be seen, and FIG. 8D shows a summary of different experiments, wherein in particular the percentage of all microscopic visible particles is shown according to the number of cells of which they consist. These experiments show that by temporally limited action of high liquid shear stress on tumor cell clusters CTCC these can be destroyed, so that only tumor single cells CTCs are present. With greater shear stress, even the individual tumor cells CTCs are destroyed.

These experiments also showed that the destruction of the tumor cell clusters CTCC or tumor single cell CTCs correlated directly with two parameters: on the one hand the height of the liquid shear stress (the shearing stress), and on the other hand the duration of the action of the shear stress. Higher shear stress with shorter dwell time in the pump 2 led to the same inactivating effect of the pump 2 as lower shear stress with longer dwell time in the pump 2. This allows a control of the pump 2 within a wide therapeutic range in that the pressure on the input side and output side of the pump 2 and the differential pressure is kept at 0 by means of a control unit. With increased blood flow, the speed is up-regulated. As a result, more liquid is pumped through the pump 2, thus reducing the dwell time on the throttle 13. At the same time, the shear stress increases. As long as the pump characteristic can be linearized with sufficient accuracy, the destructive effect of the device according to the invention remains approximately constant. The control unit can work autonomously and thus ensures that the device according to the invention can adapt to the local circulation control in the body. In particular, a negative impact on the blood circulation of the patient's body as well as congestion and local or even systemic hypertension is avoided. Rather, the device according to the invention appears to be non-existent to the natural blood circulation.

As already mentioned, in the context of the method according to the invention, the aim is in principle to place the device according to the invention as close as possible to the tumor-affected organ or organ part. Of course, the corresponding vein must be suitable for the appropriate placement of the pump 2 in terms of size and accessibility. In addition, the physiological conditions or medical reasons can call for a particular location of placement of the pump 2 according to the invention in venous drain VA of an organ or organ part, as will be explained in FIG. 6 and FIG. 7. The hepatic portal vein (V. portae hepatis) appears to be particularly suitable, as shown in the region of FIG. 6 indicated by the arrow. The hepatic portal vein collects the venous blood from the unpaired abdominal organs such as the stomach, the small intestine via the upper mesenteric vein (V. mesenterica superior), the large intestine, and portions of the rectum through the lower mesenteric vein (V. mesenterica inferior), pancreas, and spleen via the splenic vein (V. splenica) and leads it to the liver. If the physiological requirements for this exist, the pump 2 according to the invention can be arranged in one or more of the named venous drains VA, but the placement in the hepatic portal vein reliably reduces the hematogenous metastasis due to circulating tumor cell clusters CTCC in the liver.

Furthermore, the renal vein (V. renalis), the inferior vena cava (V. cava inferior) and the superior vena cava (V. cava superior) appear to be particularly suitable for the placement of the pump 2 according to the invention, as shown in the arrowed areas of FIG. 7. In the upper vena cava, placement of the pump 2 according to the invention in the area of the venous angle (Angulus venosus) in particular appears to be particularly advantageous. The venous angle is designated in humans by the two sites (right/left half of the body) in the blood vessel system, where the jugular vein (V. jugularis interna) joins with the subclavian vein (Vena subclavia) to the brachiocephalic vein. This is also where the large lymph collecting trunks enter. The left vein angle is the more significant, since here (among others) the lymphatic collection trunk Ductus thoracicus enters, which transports lymph from the entire lower half of the body. In contrast, only a smaller lymphatic vessel, which leads lymph from the right arm, the right thorax side and the right side of the neck (Ductus lymphaticus dexter), opens into the right vein angle. In the further course, the right and left brachiocephalic veins join together to form the superior vena cava, which opens into the right atrium (see FIG. 7). Since the lymphatic collection trunks open into the venous angle, thus the probability lymphogenic metastasis is reduced at a placement of the pump 2 according to the invention in the area of the venous angle of the superior vena cava. However, it is also conceivable to place a plurality of devices according to the invention at different locations in the venous drain VA of a tumor-affected organ or organ part in order to achieve in their interaction the best possible effect for reducing the formation of metastases.

What is claimed is:

1. A method for comminution or inactivation of circulating tumor cells (CTC) or tumor cell clusters (CTCC) from a tumor-affected organ or organ part, wherein in the venous drain (VA) of the tumor-affected organ or organ part a pump with a pressure-increasing section and a pressure-reducing throttle is arranged for comminution or inactivation of circulating tumor cells or tumor cell clusters and is operated at the output side in its operating point given by volumetric flow and pumping pressure according to the volumetric flow and the blood pressure of the venous drain of the tumor-affected organ or organ part wherein the pump creates shear stress in the blood moving through the pump and, thereby, generates comminution or inactivation of the tumor cells or tumor cell clusters.

2. The method according to claim 1, wherein the pump is operated with a volumetric flow of 0.1-1.5 liters/minute.

3. The method according to claim 2, wherein the pressure before the pump and after the throttle is measured and the pressure difference of the two measured pressure values is controlled by varying the speed of the pump to a predetermined setpoint value.

4. The method according to claim 2, wherein the pump is arranged in the hepatic portal vein (V. portae hepatis), in the renal vein (V. renalis), in the inferior vena cava (V. cava inferior) and/or the superior vena cava (superior vena cava).

5. The method according to claim 1, wherein the pump is operated with a pumping pressure of 4-20 hPa.

6. The method according to claim 5, wherein the pressure before the pump and after the throttle is measured and the pressure difference of the two measured pressure values is controlled by varying the speed of the pump to a predetermined setpoint value.

7. The method according to claim 5, wherein the pump is arranged in the hepatic portal vein (V portae hepatis), in the renal vein (V. renalis), in the inferior vena cava (V. cava inferior) and/or the superior vena cava (superior vena cava).

8. The method according to claim 1, wherein the pressure before the pump and after the throttle is measured and the pressure difference of the two measured pressure values is controlled by varying the speed of the pump to a predetermined setpoint value.

9. The method according to claim 8, wherein the setpoint value predetermined for the pressure difference is 0.

10. The method according to claim 9, wherein the pump is arranged in the hepatic portal vein (V portae hepatis), in the renal vein (V. renalis), in the inferior vena cava (V. cava inferior) and/or the superior vena cava (superior vena cava).

11. The method according to claim 8, wherein the pump is arranged in the hepatic portal vein (V portae hepatis), in the renal vein (V. renalis), in the inferior vena cava (V. cava inferior) and/or the superior vena cava (superior vena cava).

12. The method according to claim 1, wherein the pump is arranged in the hepatic portal vein (V. portae hepatis), in the renal vein (V. renalis), in the inferior vena cava (V. cava inferior) and/or the superior vena cava (superior vena cava).

13. The method according to claim 12, wherein the pump is arranged in the upper vena cava in the region of the vein angle (Angulus venosus).

14. A method for comminution or inactivation of circulating tumor cells (CTC) or tumor cell clusters (CTCC) from a tumor-affected organ or organ part utilizing a pump arranged in the venous drain of a tumor-affected organ or organ part, said pump having a pressure-increasing section and a pressure-reducing throttle for a volumetric flow and pumping pressure corresponding on the output side to the volumetric flow and the blood pressure of the venous drain of the tumor-affected organ or organ part for comminuting or inactivating circulating tumor cells (CTC) or tumor cell clusters (CTCC) from the tumor-affected organ or organ part by shear stresses exerted on the blood moving through the pump.

15. The method according to claim 14, wherein the pump is operated with a pumping pressure of 4-20 hPa.

16. The method according to claim 15, wherein the pressure before the pump and after the throttle is measured and the pressure difference of the two measured pressure values is controlled by varying the speed of the pump to a predetermined setpoint value.

* * * * *